(12) United States Patent
Dang et al.

(10) Patent No.: US 10,492,779 B2
(45) Date of Patent: Dec. 3, 2019

(54) SUTURING DEVICES FOR HEART VALVE SURGERY

(71) Applicant: Edwards Lifesciences Corporation, Irvine, CA (US)

(72) Inventors: Kevin K. Dang, Garden Grove, CA (US); Bryan A. Janish, Huntington Beach, CA (US); Manouchehr A. Miraki, Laguna Hills, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 123 days.

(21) Appl. No.: 15/895,950

(22) Filed: Feb. 13, 2018

(65) Prior Publication Data

US 2018/0235602 A1 Aug. 23, 2018

Related U.S. Application Data

(60) Provisional application No. 62/461,159, filed on Feb. 20, 2017.

(51) Int. Cl.
*A61B 17/04* (2006.01)
*A61B 17/062* (2006.01)
*A61B 17/06* (2006.01)
*A61F 2/24* (2006.01)
*A61B 17/00* (2006.01)

(52) U.S. Cl.
CPC ...... *A61B 17/0469* (2013.01); *A61B 17/0625* (2013.01); *A61B 17/0491* (2013.01); *A61B 2017/00243* (2013.01); *A61B 2017/00783* (2013.01); *A61B 2017/047* (2013.01); *A61B 2017/0472* (2013.01);

(Continued)

(58) Field of Classification Search
CPC .................................................. A61B 17/0469
See application file for complete search history.

(56) References Cited

U.S. PATENT DOCUMENTS 4,702,250 A * 10/1987 Ovil ........................ A61B 17/04
606/148
5,417,700 A * 5/1995 Egan ................... A61B 17/0469
606/144

(Continued)

FOREIGN PATENT DOCUMENTS

CA 2792926 A1 * 11/2011 ........... A61B 17/062
CA 2827737 A1 * 8/2012 ........... A61F 2/0095

*Primary Examiner* — Robert K Arundale
*Assistant Examiner* — Mohammed S Adam
(74) *Attorney, Agent, or Firm* — Klarquist Sparkman LLP

(57) ABSTRACT

Disclosed are devices and methods for delivering several sutures accurately and simultaneously around the perimeter of an annular prosthetic device (prosthetic heart valve, annuloplasty ring, etc.) to secure the prosthetic device within a native heart valve region. Devices can comprise a proximal handle portion including an actuator and a distal suturing portion including several curved and straight needles arrayed around the shaft axis. The straight needles and the curved needles are configured to simultaneously guide a plurality of sutures through the native tissue and through the annular prosthetic device. The actuator can cause the straight needles to move axially relative to the curved needles and can also cause the curved needles to rotate, such that the motions are coordinated to simultaneously place all the sutures.

15 Claims, 14 Drawing Sheets

(52) U.S. Cl.
CPC .............. *A61B 2017/0495* (2013.01); *A61B 2017/0608* (2013.01); *A61B 2017/06028* (2013.01); *A61F 2/2409* (2013.01)

(56) References Cited

U.S. PATENT DOCUMENTS

| | | | | |
|---|---|---|---|---|
| 5,545,171 | A * | 8/1996 | Sharkey | A61B 17/0469 606/139 |
| 5,735,862 | A * | 4/1998 | Jennings | A61B 17/0491 112/169 |
| 5,860,992 | A * | 1/1999 | Daniel | A61B 17/0469 606/139 |
| 6,206,894 | B1 * | 3/2001 | Thompson | A61B 17/062 606/144 |
| 6,280,460 | B1 * | 8/2001 | Bolduc | A61B 17/0469 606/144 |
| 6,464,707 | B1 * | 10/2002 | Bjerken | A61B 17/0469 606/139 |
| 7,182,771 | B1 * | 2/2007 | Houser | A61B 17/0644 606/155 |
| 7,445,626 | B2 * | 11/2008 | Songer | A61B 17/0057 606/224 |
| 7,670,370 | B2 * | 3/2010 | Hill | A61B 17/0469 623/2.11 |
| 7,674,271 | B2 * | 3/2010 | Bjerken | A61B 17/00234 606/144 |
| 8,663,249 | B2 * | 3/2014 | Badhwar | A61B 17/062 606/144 |
| 8,790,290 | B2 * | 7/2014 | Viola | A61B 17/0643 604/164.01 |
| 2001/0021856 | A1 * | 9/2001 | Bolduc | A61B 17/0469 606/144 |
| 2002/0049453 | A1 * | 4/2002 | Nobles | A61B 17/0057 606/139 |
| 2002/0058994 | A1 * | 5/2002 | Hill | A61B 17/0469 623/2.11 |
| 2011/0245850 | A1 * | 10/2011 | van der Burg | A61B 17/0401 606/145 |
| 2011/0270279 | A1 * | 11/2011 | Badhwar | A61B 17/062 606/144 |
| 2011/0301701 | A1 * | 12/2011 | Padala | A61B 17/1155 623/2.11 |
| 2012/0239142 | A1 * | 9/2012 | Liu | A61F 2/0095 623/2.11 |
| 2012/0271322 | A1 * | 10/2012 | Mohamed | A61B 17/0469 606/144 |
| 2013/0030520 | A1 * | 1/2013 | Lee | A61F 2/2433 623/2.11 |
| 2014/0303654 | A1 * | 10/2014 | Nobles | A61B 17/0469 606/147 |
| 2016/0045313 | A1 * | 2/2016 | Miraki | A61F 2/2448 623/2.37 |
| 2016/0213372 | A1 * | 7/2016 | Eliachar | A61B 17/0469 |
| 2017/0135692 | A1 * | 5/2017 | Belson | A61B 17/0057 |
| 2017/0252032 | A1 * | 9/2017 | Hiorth | A61B 17/0401 |
| 2018/0296339 | A1 * | 10/2018 | McLean | A61F 2/2439 |
| 2019/0150915 | A1 * | 5/2019 | Sauer | A61B 17/0469 |

* cited by examiner

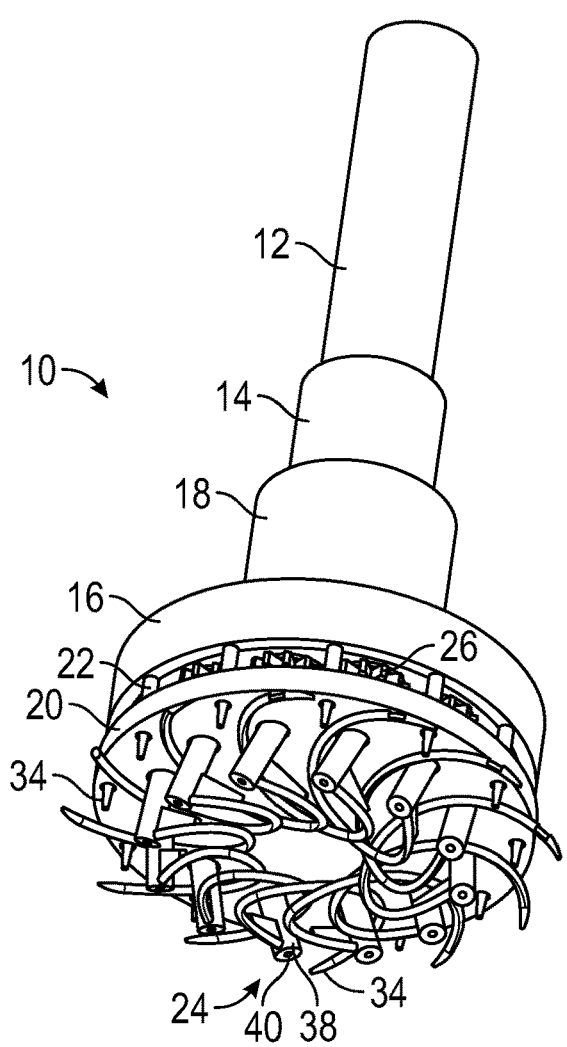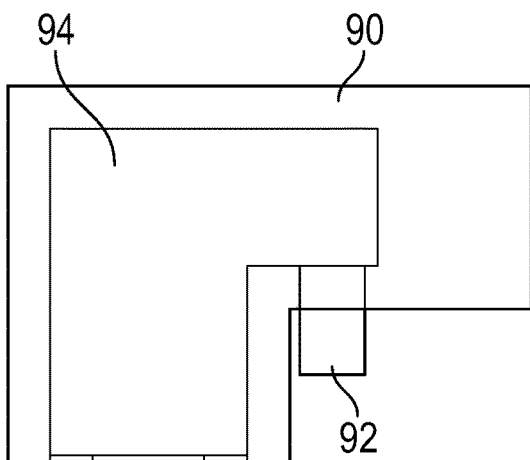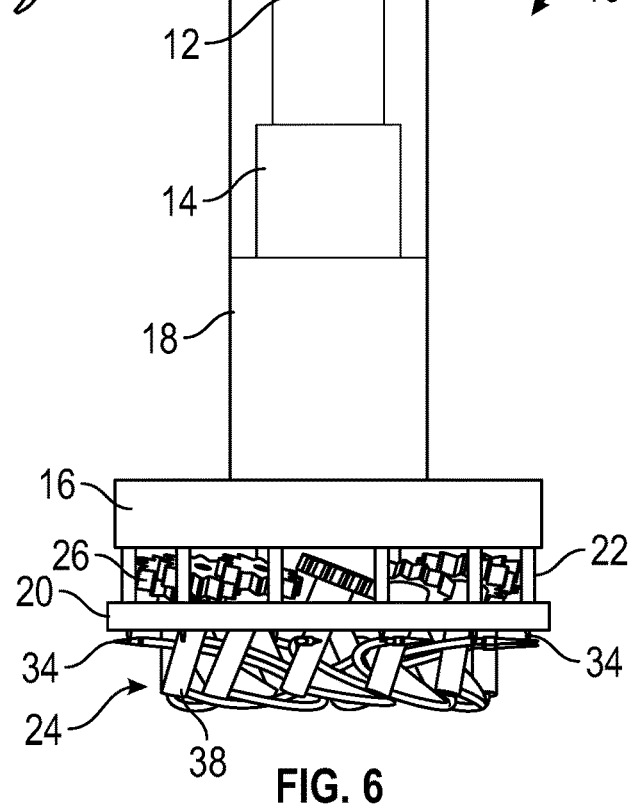

SUTURING DEVICES FOR HEART VALVE SURGERY

CROSS-REFERENCE TO RELATED APPLICATIONS

This application claims the benefit of U.S. Patent Application No. 62/461,159 filed Feb. 20, 2017, which is incorporated by reference herein in its entirety.

FIELD

This application is related to devices and methods for suturing prosthetic devices during heart valve surgeries.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death.

Treatments for such disorders include surgical repair or replacement of the valve, such as during open heart surgery. In some procedures, a new prosthetic heart valve is sutured within the valve region to replace the functionality of the native valve. In other procedures, an annuloplasty ring or other device is sutured around the native valve annulus to improve the functionality of the native valve. In many of these surgeries, a series of many sutures need to be placed around the perimeter of the prosthetic device to secure it to the native tissue.

Traditionally, each suture is placed one at a time by a surgeon, which requires a lot of time and requires great care and dexterity to ensure that each suture is secured properly. If any of the sutures come loose, or are too tight or too loose, the patient's health may be jeopardized. At the same time, it is desirable to minimize the duration of the surgical process to reduce the risks of complications such as infection and ischemia. Thus, there is a need for devices and methods that enable a prosthetic heart valve device to be sutured in place both more rapidly and more accurately.

SUMMARY

Disclosed herein are several exemplary suturing device and related methods for delivering several sutures accurately and simultaneously around the perimeter of an annular prosthetic device (e.g., a prosthetic heart valve, an annuloplasty ring, or other annular device) to secure the prosthetic device within a native heart valve region. Exemplary suturing devices can comprise a shaft portion defining a shaft axis, a handle portion at a proximal end of the shaft portion, the handle portion including an actuator, and a suturing portion at a distal end of the shaft portion. The suturing portion includes several curved needles arrayed around the shaft axis and a corresponding number of straight needles arrayed around the shaft axis. The straight needles and the curved needles are configured to guide a plurality of sutures through the native tissue and through the annular prosthetic device simultaneously. In some embodiments, the actuator causes the straight needles to move axially relative to the curved needles and also causes the curved needles to rotate, such that the axial motion of the straight needles and the rotation of the curved needles are coordinated to simultaneously place the plurality of sutures that secure the annular prosthetic device within the native heart valve region.

The disclosed device can be used to suture a prosthetic device in any of the native heart valve regions, and particularly in the native aortic valve region. The number of sutures placed by the device can vary from one or two or three, to 10 or 20 or more. The sutures can be placed in predetermined locations and spacing around the perimeter of the prosthetic device to secure it in place.

In some embodiments, the straight needles project distally from a first rigid support plate. The first rigid support place can be mounted around a distal end of the shaft portion and proximal to the curved needles. The straight needles can penetrate distally into/through the annular prosthetic device (e.g., through a sewing ring of a prosthetic heart valve) when the actuator causes the straight needles to move axially relative to the curved needles. In some embodiments, the straight needles comprise hooks or other suture engagement members at their distal ends, to allow the straight needs to engage the sutures from the curved needles and draw the sutures back proximally through the annular prosthetic device.

In some embodiments, the curved needles each project from a different respective drive shaft, and the curved needles each rotate about an axis of their own respective drive shaft. The drive shafts can all be supported by a second rigid plate distal to the first rigid plate, such that the drive shafts can each rotate about their respective axis relative to the second rigid plate. The drive shafts can all be engaged to a common central driver (e.g. a sun gear), wherein the central driver causes all the drive shafts and all the curved needles to rotate at the same time and same rate.

The sutures can pass through or along the drive shafts and through or along the curved needles, such that the sutures are guided through the native tissue and into/adjacent to the annular prosthetic device along with the rotation of the curved needles. Once the sutures are guided into/adjacent to annular prosthetic device, the straight needles engage the plurality of sutures and pull the sutures proximally from the curved needles through the annular prosthetic device.

The foregoing and other objects, features, and advantages of the disclosure will become more apparent from the following detailed description, which proceeds with reference to the accompanying figures.

BRIEF DESCRIPTION OF THE DRAWINGS

FIG. 5 shows a perspective view of the suturing device from a distal view point.

FIG. 6 is a schematic side view of an entire suturing device including a proximal handle portion with an actuator, a shaft portion, and the distal suturing portion.

FIG. 11 also includes a cross-sectional view of the device showing one of the curved needles.

DETAILED DESCRIPTION

FIGS. 1, 2, 3A, and 4 show an annular prosthetic device 2 positioned at a desired position within the walls of a native heart valve region 4. Although the illustrated annular prosthetic device 2 is shown as a toroidal ring, it is intended to represent any of various possible annular prosthetic devices that may be sutured in place using the disclosed technology. In the case of implanting a prosthetic heart valve, for example, the illustrated annular prosthetic device 2 can represent an outer sewing ring of the prosthetic heart valve. In other procedures, the illustrated annular prosthetic device 2 can represent a flat annuloplasty ring or similar devices. Similarly, although the native heart valve region 4 is shown in FIGS. 1, 2, 3A, and 4 as a cut-away ring with a cylindrical inner wall, it is intended to represent the actual geometry of a native heart valve region (e.g., aortic valve region, pulmonary valve region, tricuspid valve region, or mitral valve region), which includes a native valve annulus of reduced inner diameter (e.g., see FIG. 20) and may include native valve leaflets and/or other native structures. The native leaflets and/or other native structures may be excised prior to implantation of the prosthetic device in many procedures. The prosthetic annular device is often sutured directly to the native valve annulus (e.g., see FIG. 12), or is otherwise positioned near to the native valve annulus.

Figure 1:
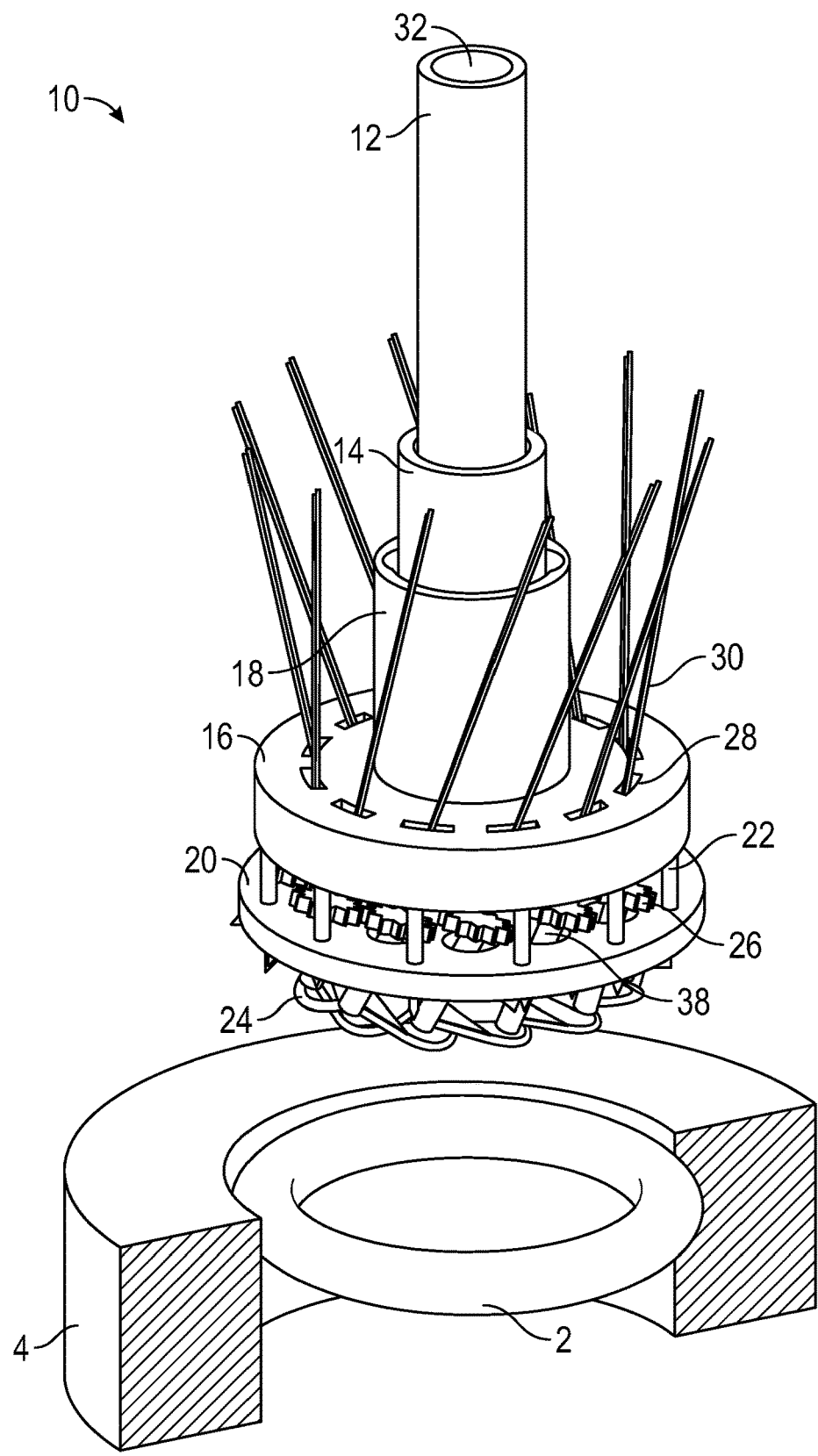
FIG. 1 illustrates a distal portion of an exemplary suturing device for implanting an annular prosthetic device within a native heart valve region.
Figure 2:
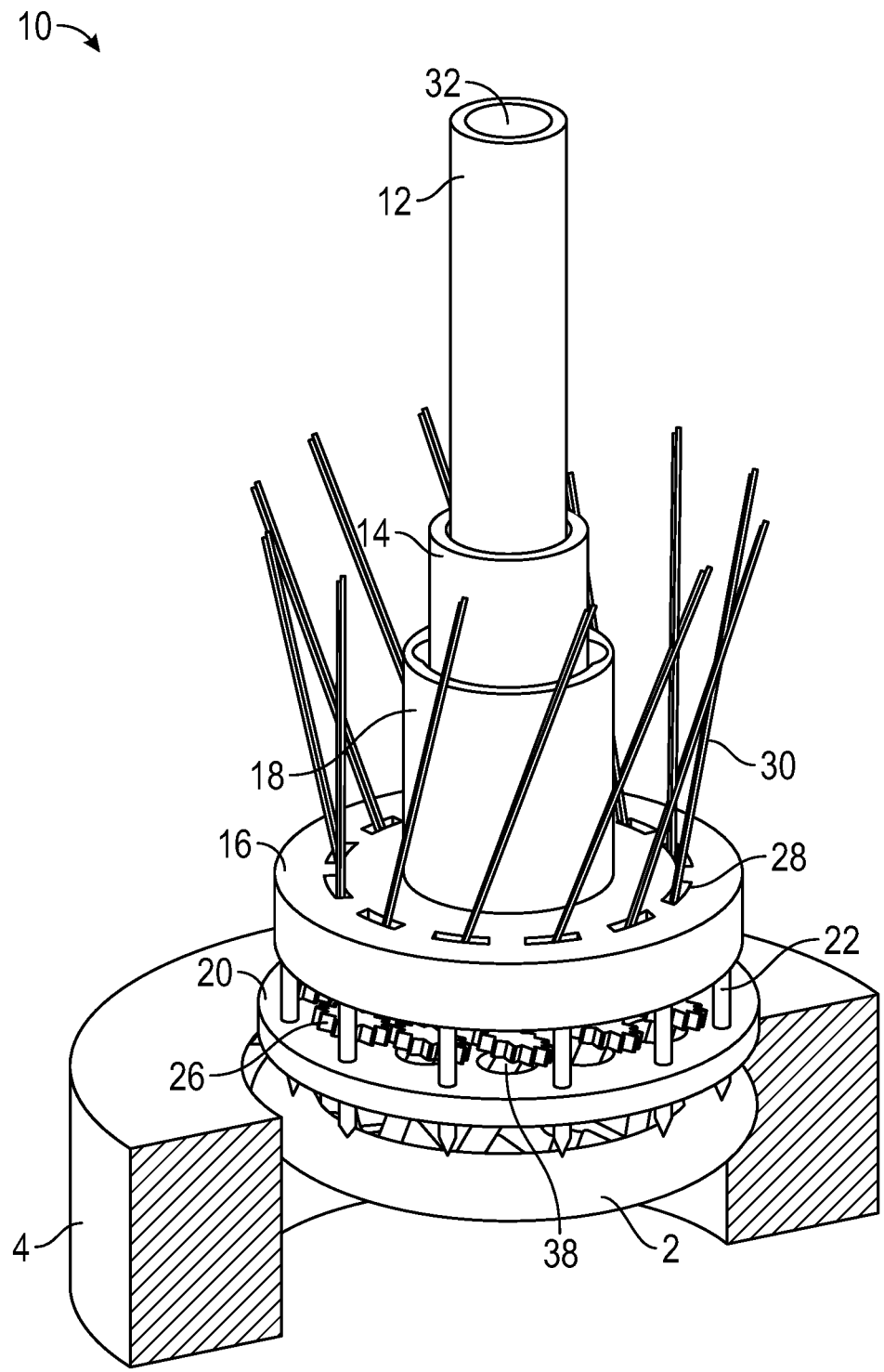
FIG. 2 shows the device of FIG. 1 positioned adjacent to an annular prosthetic device within a native heart valve region where the annular prosthetic device is to be sutured.
Figure 3A:
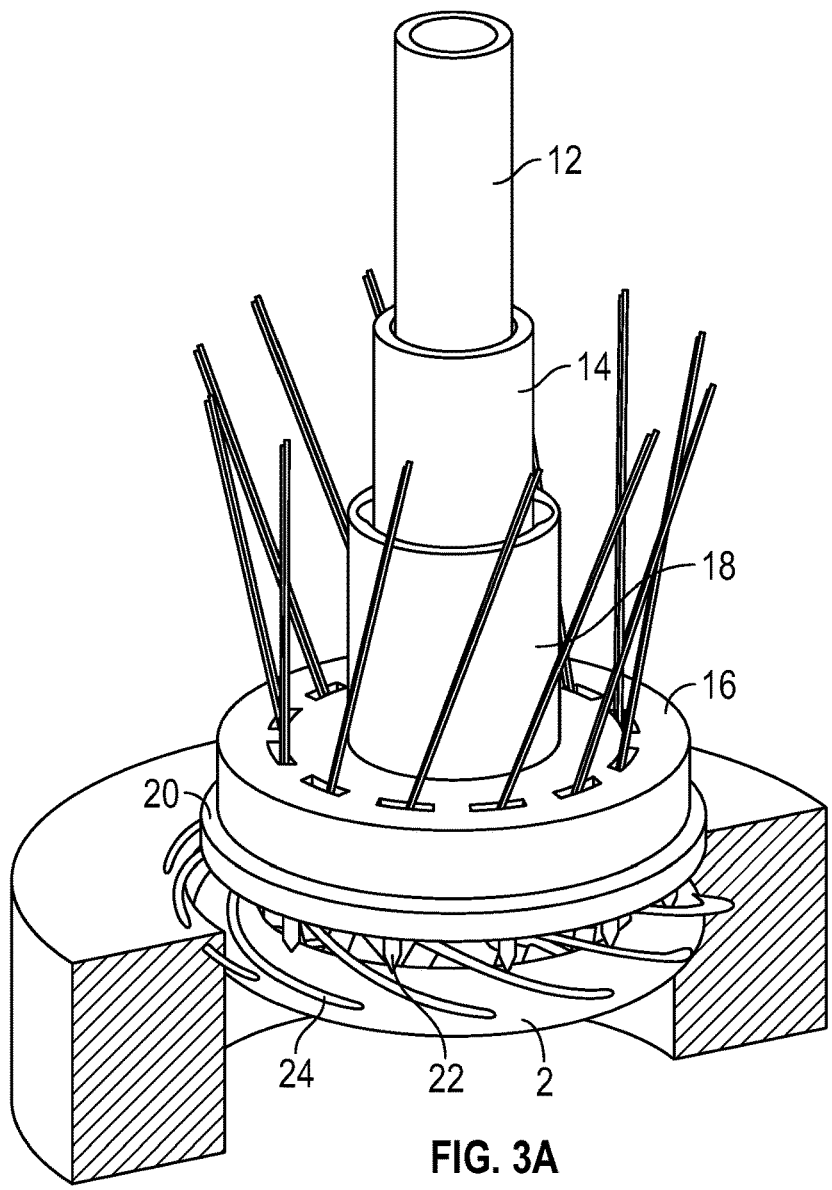
FIG. 3A shows the device of FIGS. 1 and 2 actuating to cause needles to guide several sutures simultaneously into place to secure the annular prosthetic device to the native tissue.

FIG. 1 shows the distal suturing portion of an exemplary suturing device 10 in proximity to the annular prosthetic device 2 that is to be sutured to the native heart valve region 4. The suturing device 10 is shown in various views in FIGS. 1-9. In FIG. 1, the suturing device 10 is directed toward the implantation site along the axial direction of the native heart valve, generally perpendicular to the plane of the native valve annulus. The annular prosthetic device 2 may be placed in the native heart valve region 4 prior to the suturing device 10 being introduced, or in other embodiments the annular prosthetic device 2 can be pre-attached to the bottom or distal end of the suturing device 10 and then introduced into the native heart valve region 4 in unison. FIG. 2 shows the suturing device 10 engaged with the annular prosthetic device 2 and positioned within the native heart valve region 4 ready for the suturing process. FIG. 3A shows an intermediate stage of the suturing process, and FIG. 4 shows a later stage of the suturing process after sutures can be placed through the native tissue and through the prosthetic device.

FIG. 6 shows an example of a whole suturing device 10 including elongated shaft portions 12 and 14, and a proximal handle portion 90 including a trigger actuator 92 and an actuation mechanism 94 within the handle and causes motion of the needles and other distal components when the actuator trigger 92 is pressed. FIG. 6 is partially schematic, and not necessarily drawn to scale. The shaft portion may be much longer, for example. The distal suturing portion can be inserted into the patient to the native heart valve region, while the handle portion 90 is held by a user outside the patient. In some examples, such a procedure can be performed during open heart surgery. In other examples, such a procedure can be performed a minimally invasive surgery. Access to the native aortic valve region, for example, can be made via an incision in the ascending aorta.

The suturing device 10 can comprise an inner shaft 12, and outer shaft 14 positioned around the inner shaft, as well as straight needles 22 and curved needles 24. The straight needles 22 can project distally from a first support member 16. The first support member 16 can comprise a disk-shape plate, for example, with the straight needles 22 arrayed around the perimeter of the first support member. The first support plate 16 can be fixed relative to a collar 18, and the collar 18 can be positioned around the distal end of the outer shaft 14. The collar 18 can be engaged with the outer shaft 14 via a mechanical interface such that rotation of the outer shaft 14 while the inner shaft 12 remains stationary causes axial motion of the collar 18, the support plate 18, and the straight needles 22 in unison relative to both the inner and outer shafts.

A second support member 20 that supports the curved needles 24 is positioned distal to the first support member 16 and is coupled in a fixed relationship to distal end of the inner shaft 12. When the outer shaft 14 rotates relative to the inner shaft 12, the first support member 16 and the straight needles 22 move axially relative to the second support member 20. In some embodiments, the second support plate 20 can include apertures that the straight needles 22 move through.

The second support member 20 supports a plurality of driver shafts 38 from which the curved needles 24 extend. The drive shafts 38 can extend through openings in the second support member 20 that allow the drive shafts to each rotate about their own individual drive shaft axis and restrict other motion of the drive shafts relative to the second support member 20. Rotation of the drive shafts 38 also causes the curved needles 24 to rotate about the respective drive shaft axes. Each of the drive shafts 38 can include a proximal head 26 configured to be rotationally driven by a common central driver 70. For example, the heads 26 can comprise an array of planetary gears and the common central driver 70 can comprise a larger diameter sun gear that is engaged with all the planetary gears at the same time. The central driver 70 can be fixedly coupled to the distal end of the outer shaft 14, such that rotation of the outer shaft 14 relative to the inner shaft 12 causes the central driver 70 to rotate in the same direction, which in turn causes the heads 26, the drive shafts 38, and the curved needles 24 to rotate the opposite direction relative to the second support member 20.

Figure 8:
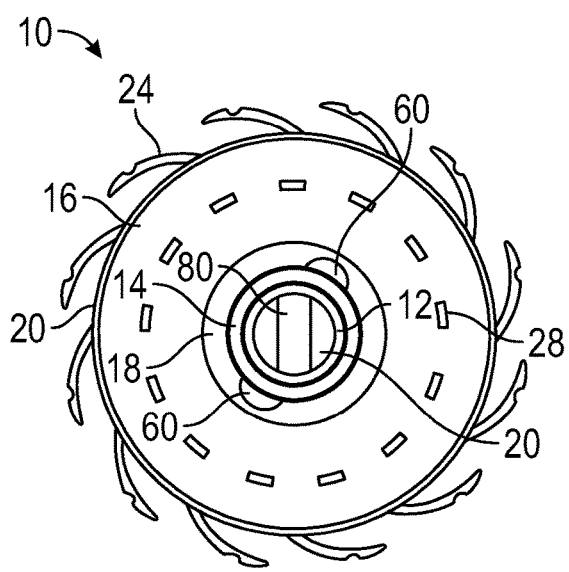
FIG. 8 is a plan view of the suturing portion of the device from a proximal view point, with curved needles partially deployed.
Figure 9:
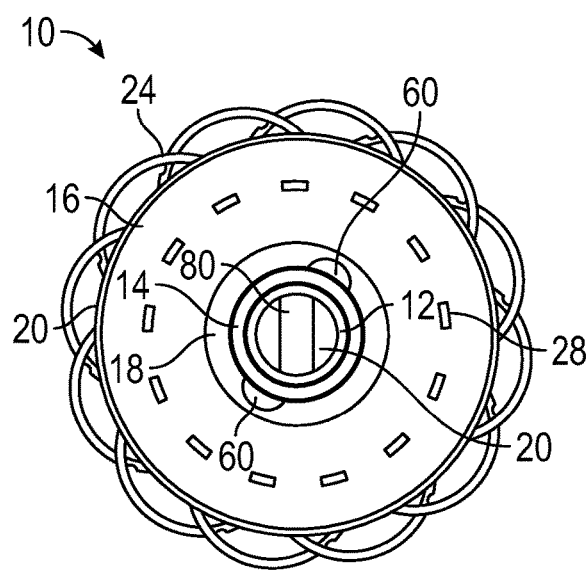
FIG. 9 is a plan view of the suturing portion of the device from a proximal view point, with curved needles fully deployed.

Thus, the same rotation of the outer shaft 14 relative to the inner shaft 12 can cause simultaneous actuation of the straight needles and the curved needles. Rotation of the outer shaft 14 in one direction causes the tips of the curved needles to rotate radially outwardly and distally (see FIG. 3A) through native tissue and then back radially inwardly below the annular prosthetic device 2, and simultaneously causes the tips of the straight needles 22 to move distally and penetrate through the annular prosthetic device 2 to a point adjacent to the tips of the curved needles (see FIG. 3B). Then, rotation of the outer shaft 14 in the opposite direction relative to the inner shaft 12 reverses the motions of the needles, allowing hooks 34 at the tips of the straight needles to engage sutures 30 from the curved needles and pull the sutures back proximally through the annular prosthetic device. Looking distally from the shaft portion of the device, FIG. 8 shows the curved needles 24 partially rotated such that the tips of the curved needles are at or near their maximum radial position, and FIG. 9 shows the curved needles fully rotated around such that the curved needles arc back underneath the second support member 20.

Figure 3B:
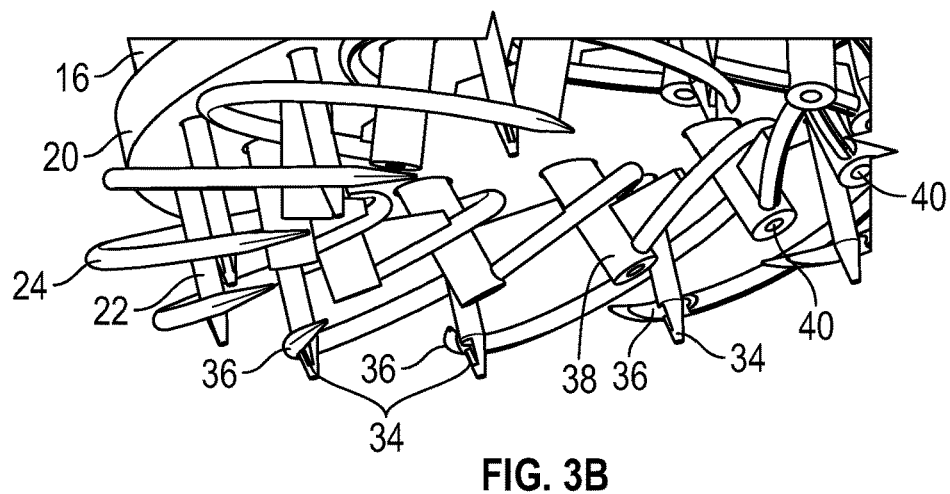
FIG. 3B is a detailed view of the several curved and straight needles of the suturing device.
Figure 3C:
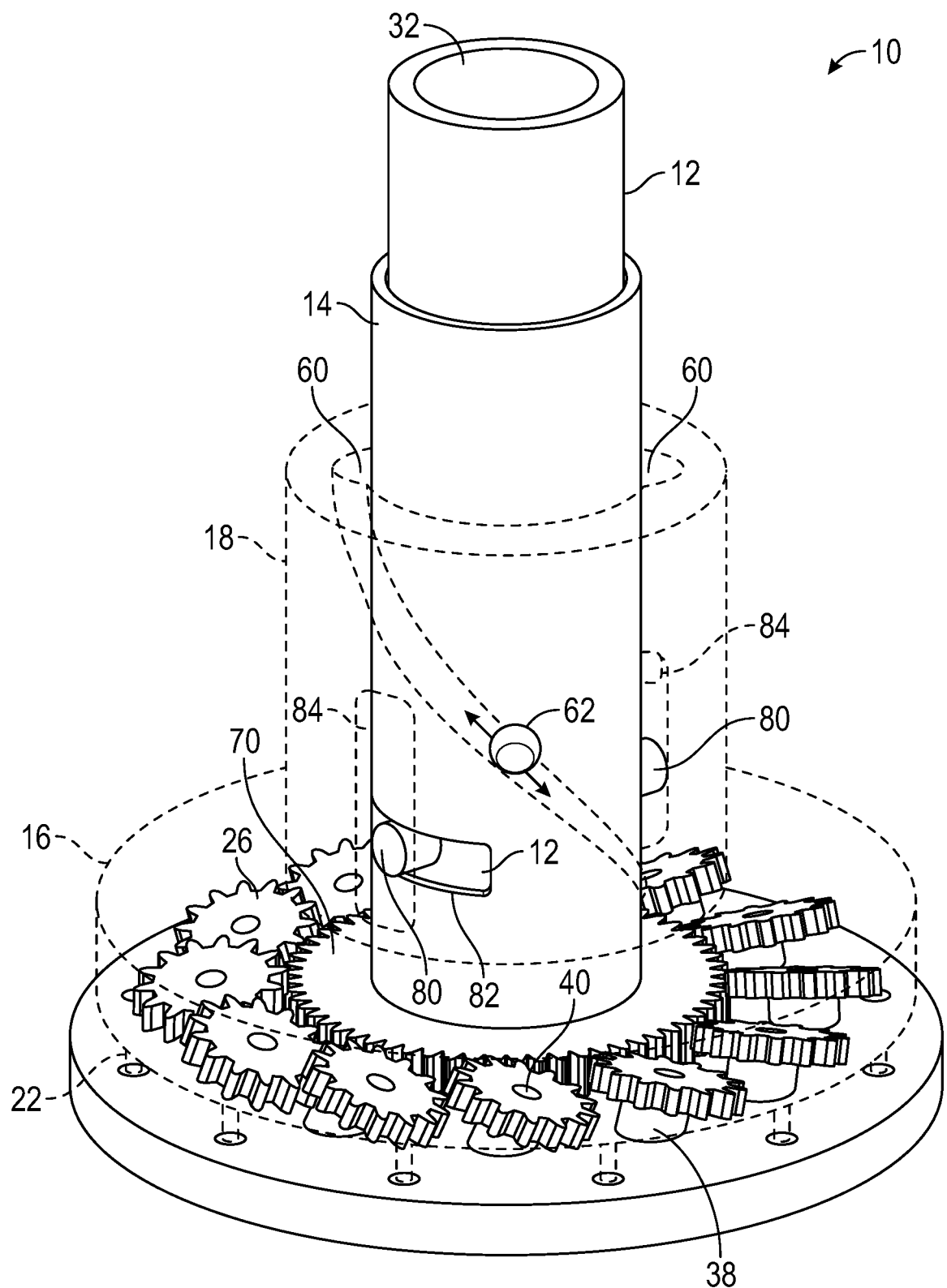
FIG. 3C illustrates internal actuation components of the suturing device, with some exterior components shown transparent.
Figure 4:
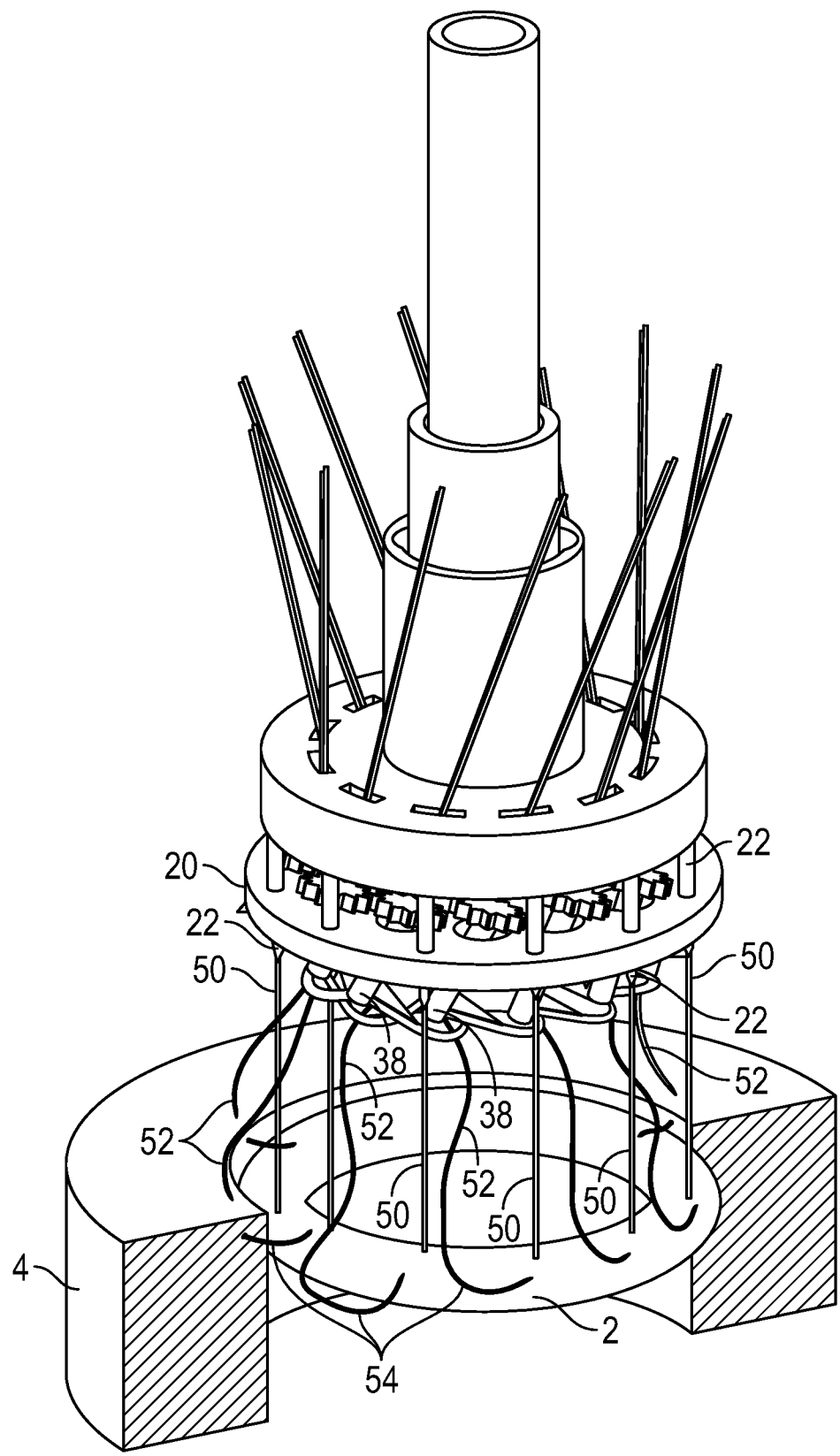
FIG. 4 shows the several sutures still suspended from the suturing device after having been guided through the native tissue and the prosthetic device, prior to suture securement.
Figure 7:
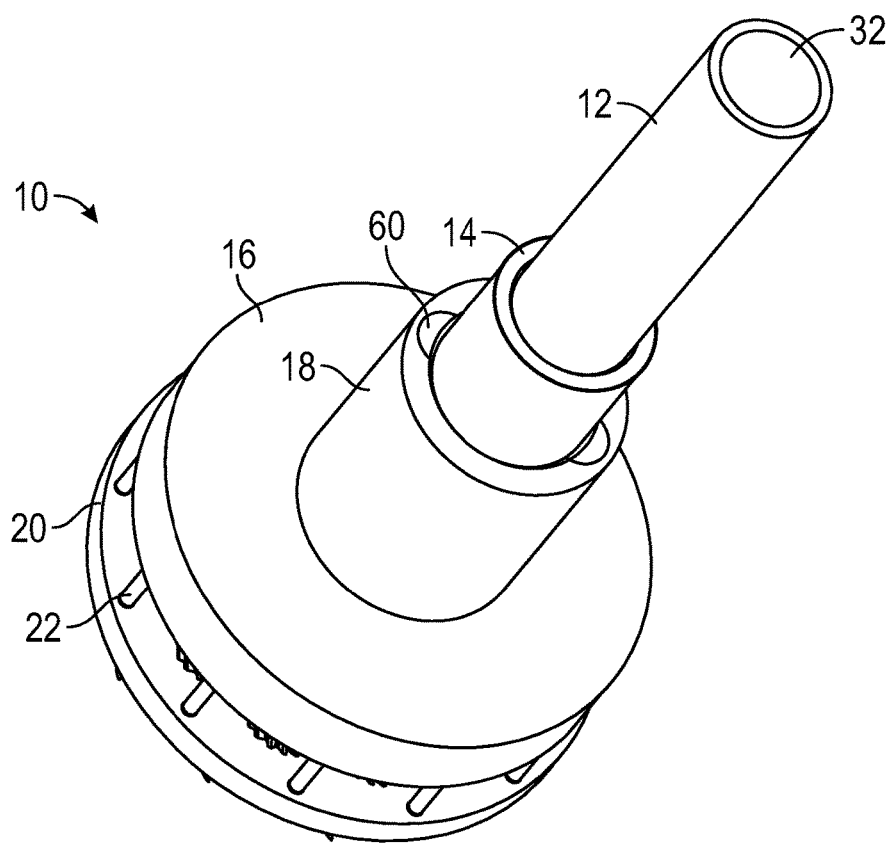
FIG. 7 shows a perspective view of the suturing device from a proximal view point.

To enable the curved needles 24 to move both radially and axially at the same time when they rotate, the drive shafts 38 can be oriented at a non-perpendicular, non-parallel angle relative to the plane of the second support member 20 and the shaft axis (as shown in FIGS. 3B and 3C).

As best shown in FIG. 3B, each of the drive shafts 38 can include a lumen 40 extending the length of the drive shaft to guide the sutures 30. The curved needles 24 can also include lumens extending from the drive shafts 38 to near the tips of the curved needles, so that the sutures can also run through the curved needles. Near the tips, the curved needles can include notches 36 that expose the sutures within the curved needles. The notches allow the hooks 34 at the ends of the straight needles to engage the sutures 30 and pull them away from the curved needles. In some embodiments, the curved needles can also include slits running along some or all of the length between the notch 36 and the drive shaft lumen 40. Such slits can allow the sutures 30 to exit the curved needles laterally after the straight needles pull the sutures away from the notches and the curved needles are rotated back the other direction and retracted. As shown in FIG. 4, this can allow the a first portion 50 of the sutures to extend from the hooks 34 of the straight needles 22 to the annular prosthetic device 2, a second portion 54 of the sutures to extend from the annular prosthetic device 2 into the native tissue 4, a third portion 52 of the sutures to extend from the native tissue 4 into the bottom openings of the drive shaft lumens 40, and then a remaining portion of the sutures to extend through the drive shafts 38 and up through suture guide apertures 28 in the first support member 16 to a tensioning device (which can be part of the suturing device 10 or external to it). After the sutures are thusly placed, they can be secured, such as by tying knots in the sutures or by applying suture securement clips or other retainers to the sutures, and free end of the sutures can be trimmed away.

FIG. 3C illustrates an exemplary mechanical interface between the collar 18, the outer shaft 14, and the inner shaft 12 that converts rotational motion of the outer shaft into axial motion of the collar, the first support member 16, and the straight needles 22. The collar 18 can include one or more helical grooves 60 on an inner surface of the collar (e.g., two opposing helical grooves) and the outer shaft 14 can include a corresponding one or more radial protrusions 62 that slide along the helical grooves 60. At the same time, the outer shaft 14 can include one or more horizontal/circumferential slots 82 and the inner shaft 12 can include a corresponding one or more projections 80 (or a single rod extending across the diameter of the inner and outer shafts and projecting from both sides) that extend through the slots 82, which restricts the outer shaft from moving axially relative to the inner shaft, while allowing the outer shaft to rotate to a limited degree (the angular width of the slots 82) relative to the inner shaft. The collar 18 can also include one or more vertical grooves 84 on its inner surface that receive the projections 80 and permit only limited vertical motion of the collar relative to the inner shaft.

When the outer shaft 14 is rotated relative to the inner shaft 12 (e.g., by actuation mechanism 94 in the handle portion 90, see FIG. 6), the protrusion 62 slides along the helical groove 60 and urges the collar 18 to move both axially and rotationally. However, the stationary projection 80 interfacing with the vertical grooves 84 in the collar prevent the collar from rotating, which forces the collar to move only axially in response to the rotation of the outer shaft 14. The collar 18 and the first support member 16 move axially relative to the stationary second support member 20 and inner shaft 12, and the straight needles 22 move axially relative to the curved needles 24. At the same time, the rotation of the outer shaft 14 turns the central driver gear 70, which turns the planetary gear heads 26 on the drive shafts 38, which rotates each of the curved needle 24. Reversing the rotational motion of the outer drive shaft 14 causes the opposite motion of the needles.

The inner shaft 12 can be hollow, allowing for any of various additional components to extend through the inner shaft from the proximal handle portion to the distal suturing portion, and optionally out of the distal end of the device. For example, lighting conduits, camera conduits, surgical tools such and cutting or expansion devices, and/or other components can be positioned within the inner shaft 12.

In some embodiments, the annular prosthetic device 2 can be pre-mounted to the distal end of the suturing device 10. FIG. 2 shows an exemplary placement of the annular prosthetic device 2 when it is mounted on the distal end of the suturing device 10. Additional securement and release components can be included in such embodiments to hold the prosthetic device in place temporarily and then release the prosthetic device from the suturing device when desired. In some embodiments, the straight needles 22 can be pre-inserted into and/or through the annular prosthetic device 2. The curved needles 24 can be initially positioned within the radial boundaries of the annular prosthetic device 2 and/or proximal to the annular prosthetic device. When the curved needles then rotate, they can project radially outward between the second support member 20 and the annular prosthetic device 2 and then curl around distally through the tissue to a point below the annular prosthetic device. The annular prosthetic device 2 can temporarily secured to the distal end of the suturing device 10 via additional sutures that are cut by a cutting device of the suturing device 10, which can be mounted and/or actuated utilizing the hollow interior of the inner shaft and/or the space below the second support member 20 and radially inside the curved needles and drive shafts. In other embodiments, a releasable clamping mechanism can be included in the suturing device 10 that holds and releases the annular prosthetic device 2 when desired.

Figure 10:
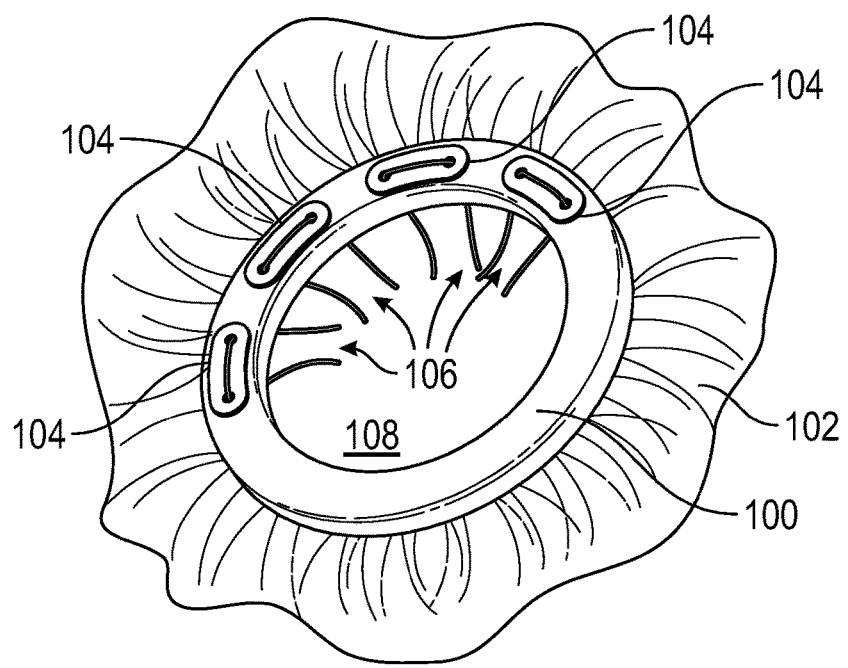
FIG. 10 shows an annular prosthetic device, such as an annuloplasty ring, partially sutured to a native valve annulus using protective pledgets.
Figure 11:
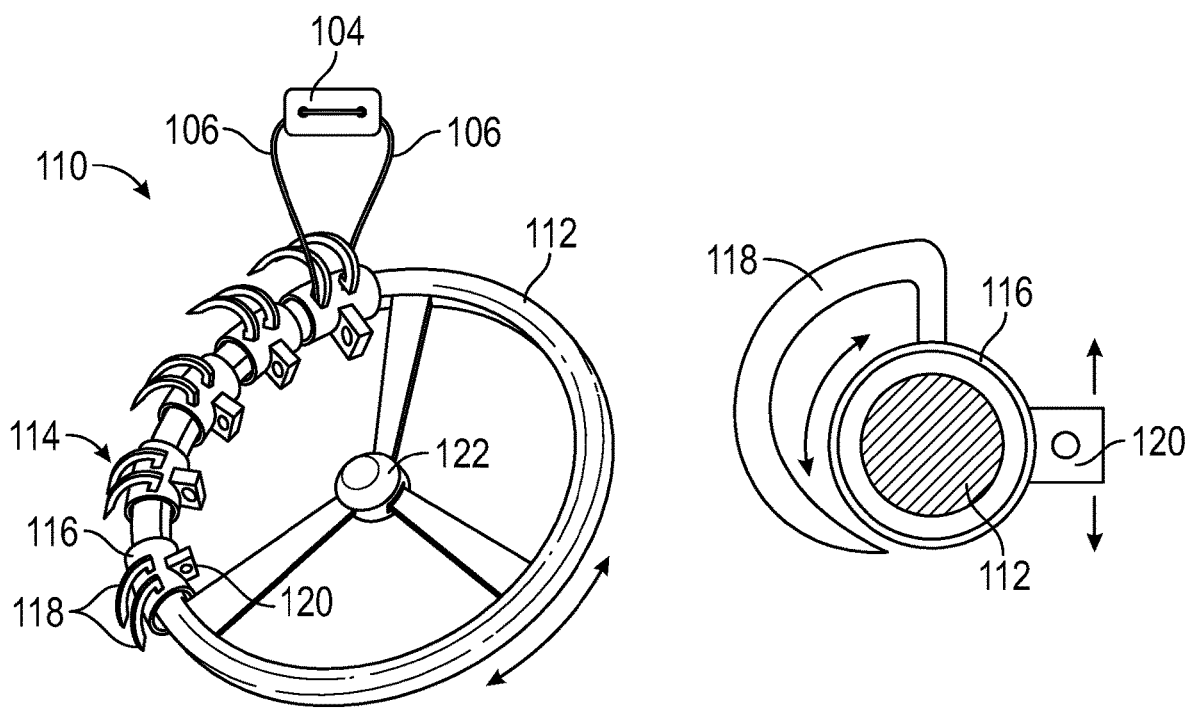
FIG. 11 shows a portion of another exemplary suturing device comprising a plurality of curved needles and configured to place several sutures simultaneously around an annular region.

FIG. 10 shows an example of an annular prosthetic device 100, in the form of an annuloplasty ring, partially sutured to a native valve annulus 102. Each suture is applied with a protective pledget 104 on one side of the device 100. FIG. 11 illustrates a portion of another exemplary suturing device 110 that includes curved needles 118 that drive sutures 106 through the annular prosthetic device 100 and the native annulus 102. The device 110 includes a central hub 122 that can be coupled to a shaft and handle. A ring 112 is coupled to the hub 122 via spokes. Needles drivers 114 are mounted on the ring 112. Each needle driver 114 includes a retainer 116 positioned around the ring 112 and a pair of curved needles 118 projecting from the retainer 116. The needles 118 can extend arcuately distally down around the ring 112 and also circumferentially around the hub 122 (e.g., counter-clockwise in FIG. 11). Each needle driver 114 can include a tab 120 that extends from the retainer 116 and is coupled to an actuation mechanism (e.g., see FIG. 13) that causes the needle drivers and curved needles to rotate in unison about the ring 112. The entire ring 112 can also spin about the central hub 122 at the same time as the needle drivers rotate to cause the needles to move circumferentially as well as the rotation motion about the ring. The needles 118 can be hollow and guide suture strands inside the needles through the prosthetic and the annulus when the needle drives rotate. The two suture strands in adjacent needles of one needle driver can form a loop that is premounted with a pledget 104, so that when the two free ends are pulled tight, the pledget 104 moves into the position shown in FIG. 10.

Figure 12:
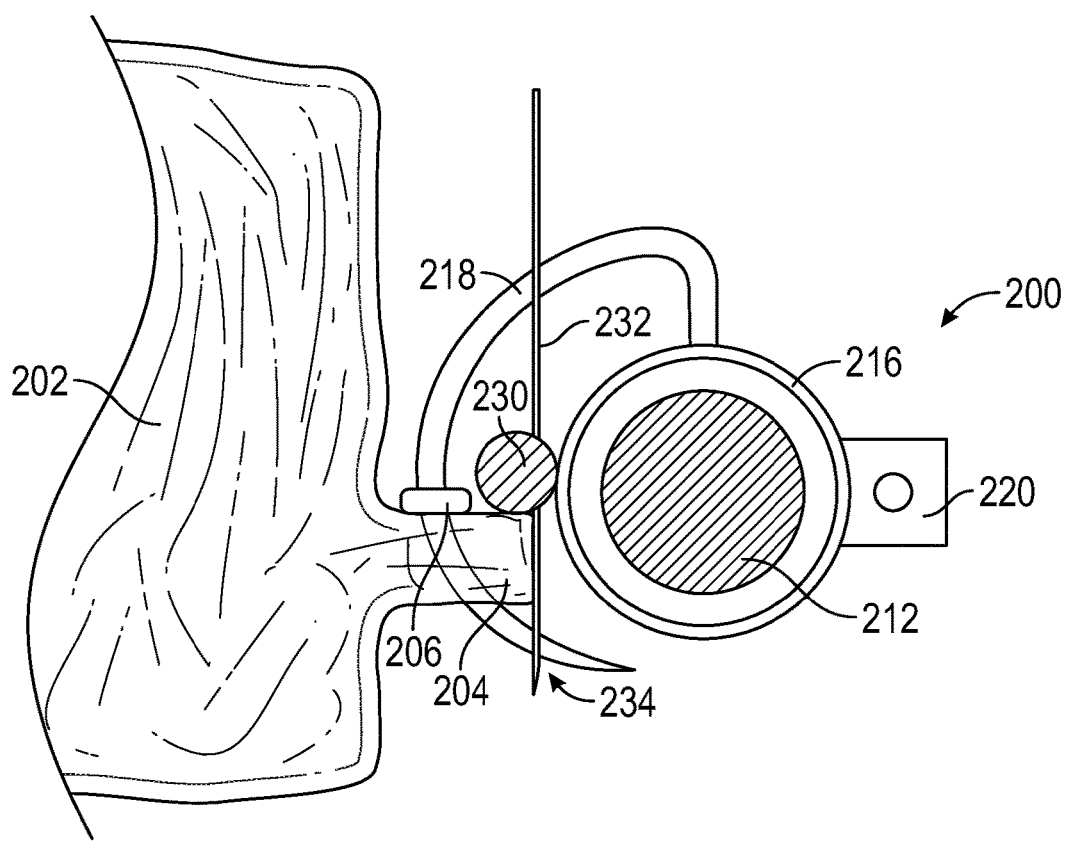
FIG. 12 is a cross-sectional side view showing the device of FIG. 12 suturing a prosthetic annular device to a native valve annulus.
Figure 13:
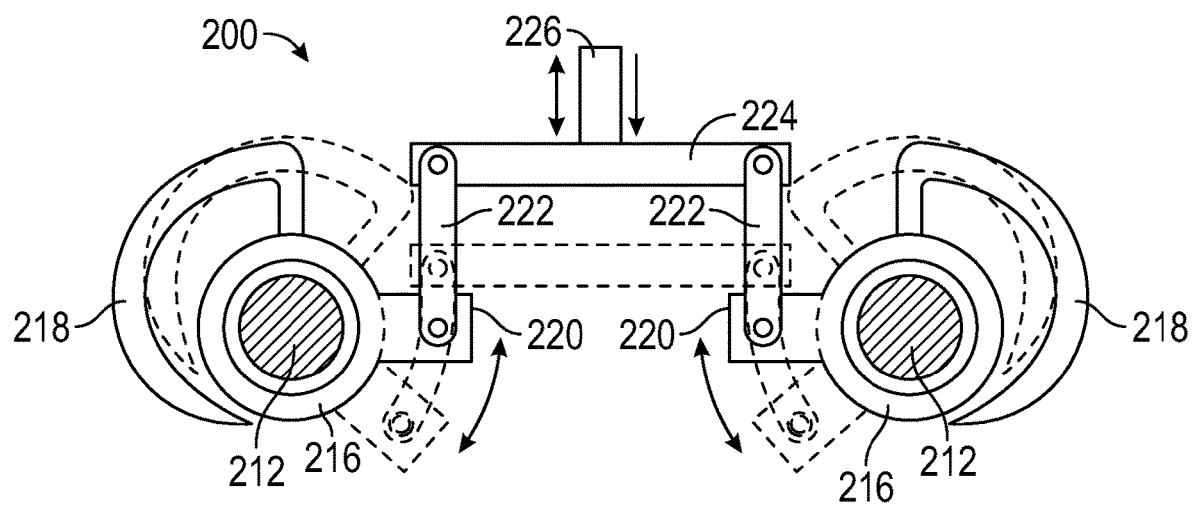
FIG. 13 shows an exemplary actuation mechanism for a suturing device similar to that shown in FIGS. 11 and 12.

FIG. 12 shows another exemplary suturing device 200 similar to the device 110. The device 200 includes ring 212 with curved needles 218, needle retainers 216, and tabs 220 similar to the device 110. In addition, the device 200 can include straight needles 232 that move axially and cooperate with the curved needles to guide sutures through the native annulus 204 and through an annular prosthetic device 230 positioned above the annulus. The curved needles and straight needles can actuate similar to the suturing device 10, where the curved needles initially guide the sutures through the native tissue and then the straight needles pull the sutures up through the annular prosthetic device. FIG. 13 shows an actuation mechanism for the suturing device 200. Shaft 226 moves axially and pushes and pulls plate 224, which is coupled to each of the tabs 220 for the several needle drivers via vertical linkages 222. When the shaft 226 moves up, the curved needles 218 rotate outwardly and downwardly, and when the shaft 226 moves down, the curved needles retract back up and in. The axial motion of the shaft 226 can be coordinated with the reverse axial motion of the straight needles 218, such that the straight and curved needles meet at the bottom below the annulus 204 for the straight needles to grab and pull the sutures from the curved needles.

Figure 14:
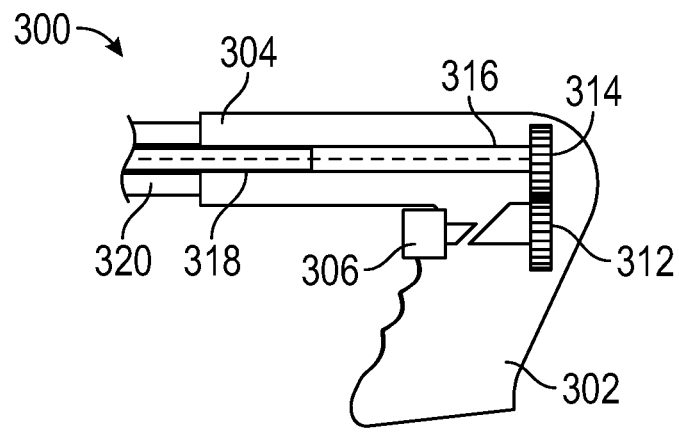
FIG. 14 is a schematic side view of a handle portion of a suturing device, including a trigger-based actuation mechanism.
Figure 15:
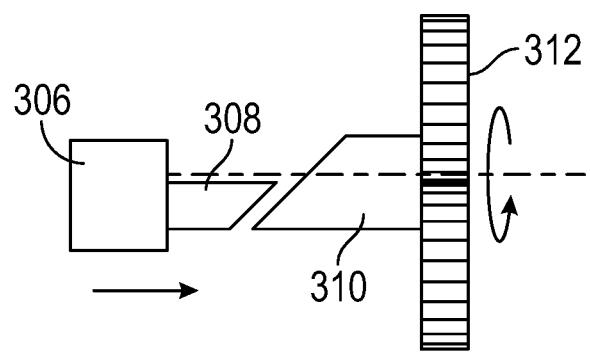
FIG. 15 illustrates a trigger-based actuator.
Figure 16:
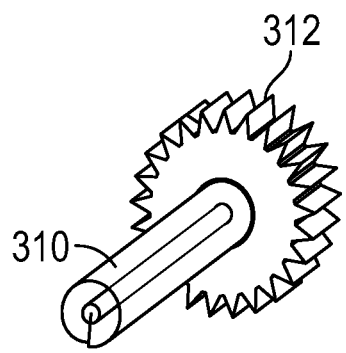
FIG. 16 shows an actuator components having a helical ramp on one end and a gear on the other end.

FIG. 14 shows an exemplary proximal portion 300 that can be used with any of the disclosed suturing devices. The proximal portion 300 includes a handle 302 and a shaft portion 304. A trigger 306 is pulled by a user to actuate the suturing device. As shown in FIGS. 15 and 16, the trigger 306 can have a shaft 308 with an inclined surface that interfaces with a helical surface of a shaft 310 fixed to a first gear 312. Pulling the trigger causes the first gear 312 to rotate. The first gear 312 drives a second gear 314, which rotates a drive shaft 316 within a fixed outer shaft 320. The drive shaft 316/318 can drive the actuation of the distal suturing portion of the device.

Figure 17:
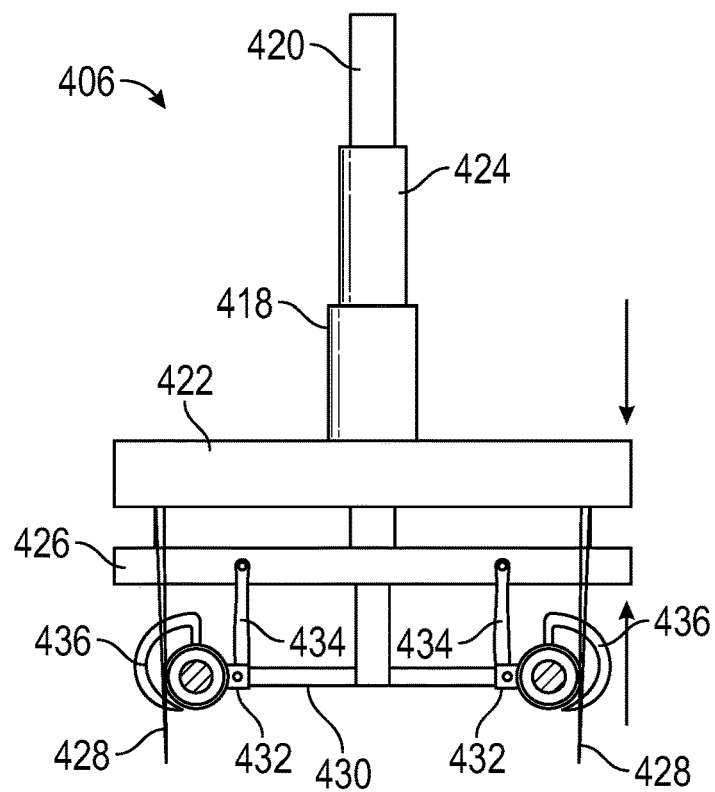
FIG. 17 is a partially cross-sectional side view of another exemplary suturing device for placing several sutures simultaneously using curved and straight needles.
Figure 18:
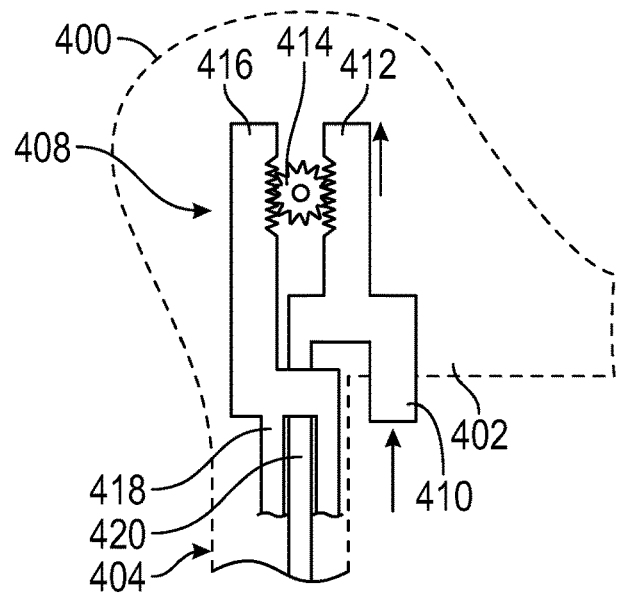
FIG. 18 shows an exemplary actuation mechanism in a handle portion for the device of FIG. 17.

FIGS. 17 and 18 illustrate another exemplary suturing device 406 comprising a proximal portion 400 (FIG. 18) with a handle 402 and shaft portion 404 coupled to the distal suturing portion (FIG. 17). The handle portion includes trigger 410 that is pulled proximally to move an inner shaft 420 and a first rack 412 proximally. The first rack 412 turns a pinion gear 414 that in turn moves a second rack 416 distally. The second rack 416 pushes an outer shaft 418 distally. As shown in FIG. 17, the inner shaft 420 is coupled to a linkages 430, 432, and 434 that rotate the curved needles 436. The outer shaft 418 is coupled to a drive plate 422 that drives the straight needles 428 axially at the same time as the curved needles rotate. The stationary handle portion 400 can be fixed relative to distal plate 426 that supports the curved needle mechanism, similar to the suturing device 10.

Figure 19:
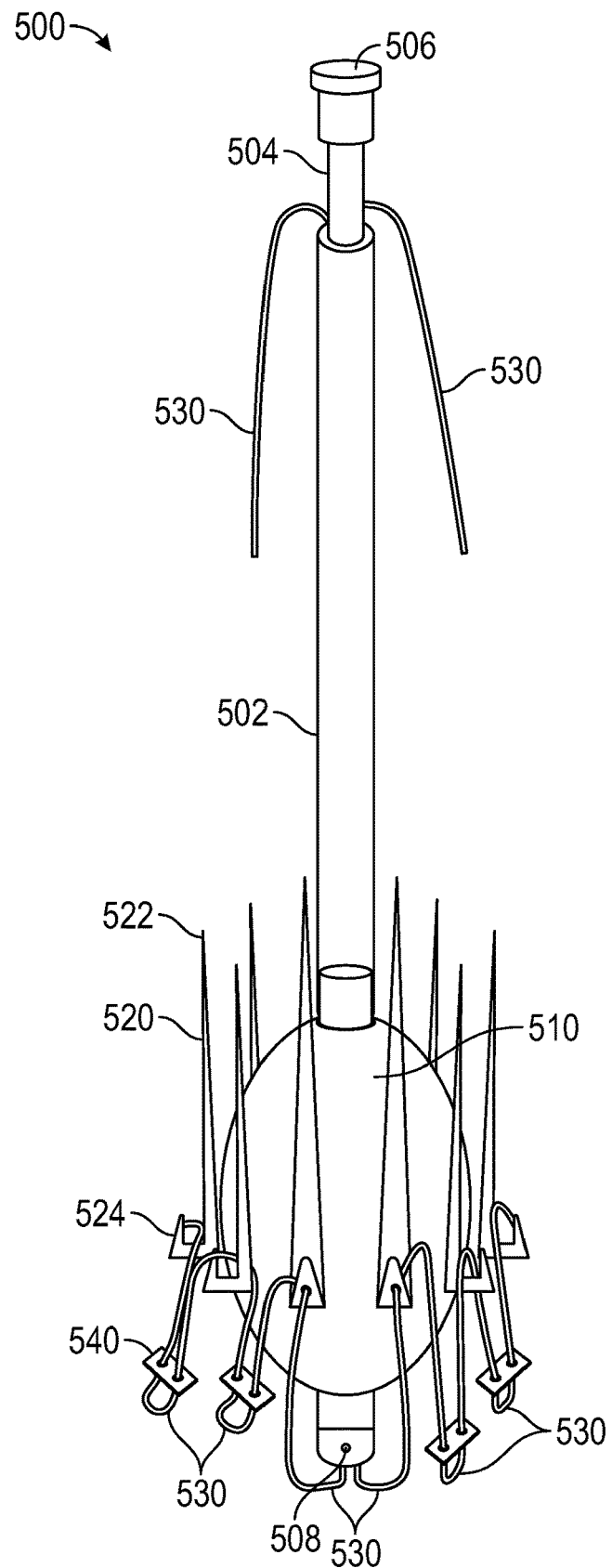
FIG. 19 shows another exemplary suturing device for placing several sutures simultaneously, using an inflatable balloon.

FIG. 19 shows another exemplary suturing device 500. The device 500 comprises an outer shaft 502, an inner shaft 504, a proximal end 506 that can be coupled to a proximal portion of the device (not shown), a distal end 508 of the device, an inflatable balloon 510, plural needles 520 mounted around the perimeter of the balloon, and one or more sutures 530 extending through the outer shaft 502, out the distal end 508, and engaged on distal hooks 524 of the needles 520. The suture 530 forms loops between the hooks 524 with a pledget optionally included on each of the suture loops. Although not shown, an annular prosthetic device can be included around the outer shaft 502 proximal to the needles 520. Alternatively, the annular prosthetic device can be pre-positioned in the desired implantation site above the annulus and then the device 500 can be inserted through both the prosthetic and the annulus.

The balloon 510 can be initially deflated when the device 500 is inserted through a native valve annulus. Once the needles 520 have cleared the annulus and the annular prosthetic device is in the desired position above the annulus, the balloon 510 can be inflated by fluid pumped through the inner shaft 504 from a proximal source. Inflation causes the needles 520 to expand radially apart to a desired array formation under the annulus. With the needles 520 in the desired position, the device can retracted proximally to drive points 522 of the needles through the annulus and through the annular prosthetic device above the annulus. Then, the balloon can be deflated and the needles detached from the balloon. Each needle can then be pulled all the way proximally through the annulus and prosthetic, pulling the sutures 530 up through the annulus and prosthetic along with the needles, and positioning the pledges below the annulus to prevent sutures pulling through the tissue.

Figure 20:
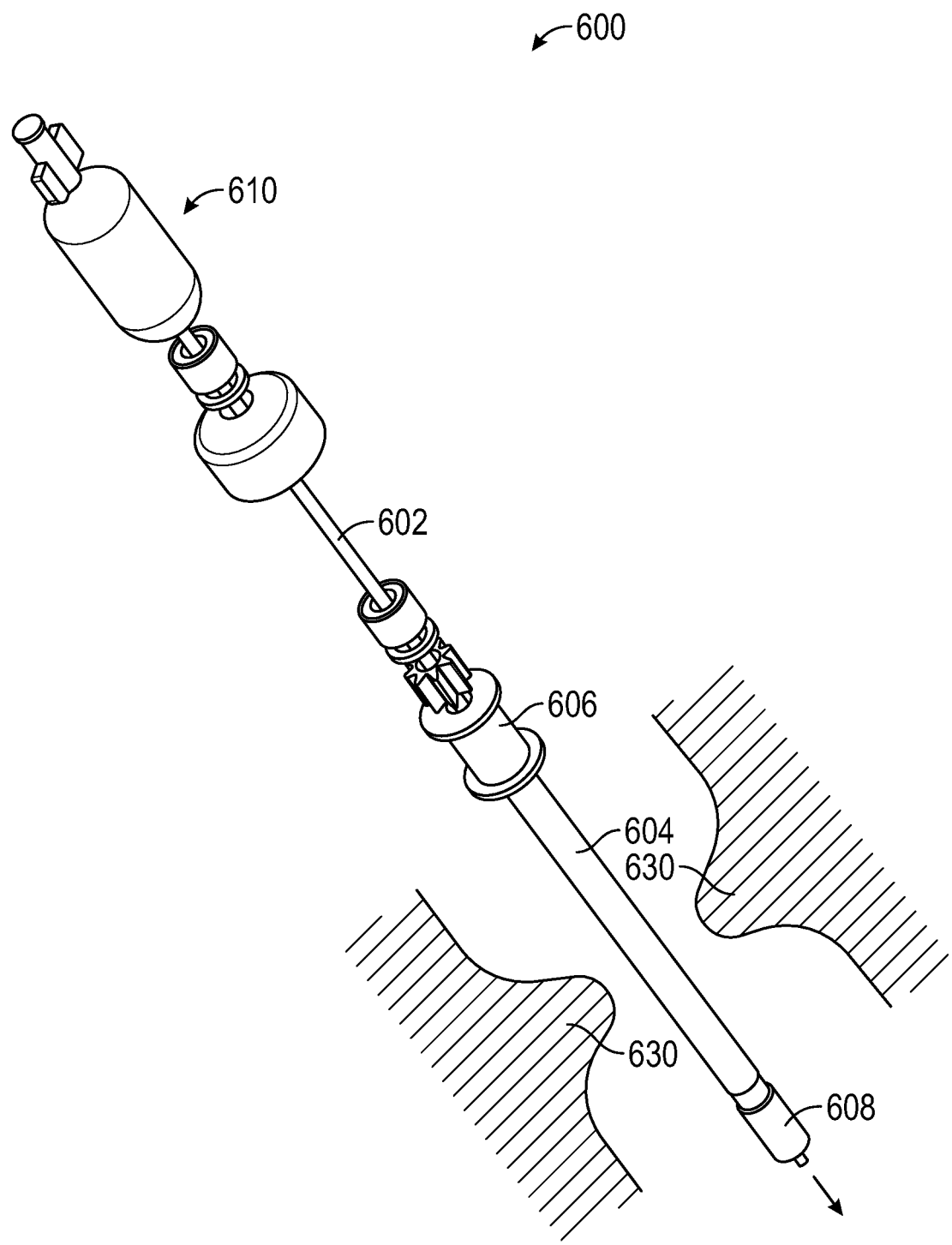
FIG. 20 shows insertion of another exemplary suturing device through a native heart valve region.
Figure 21:
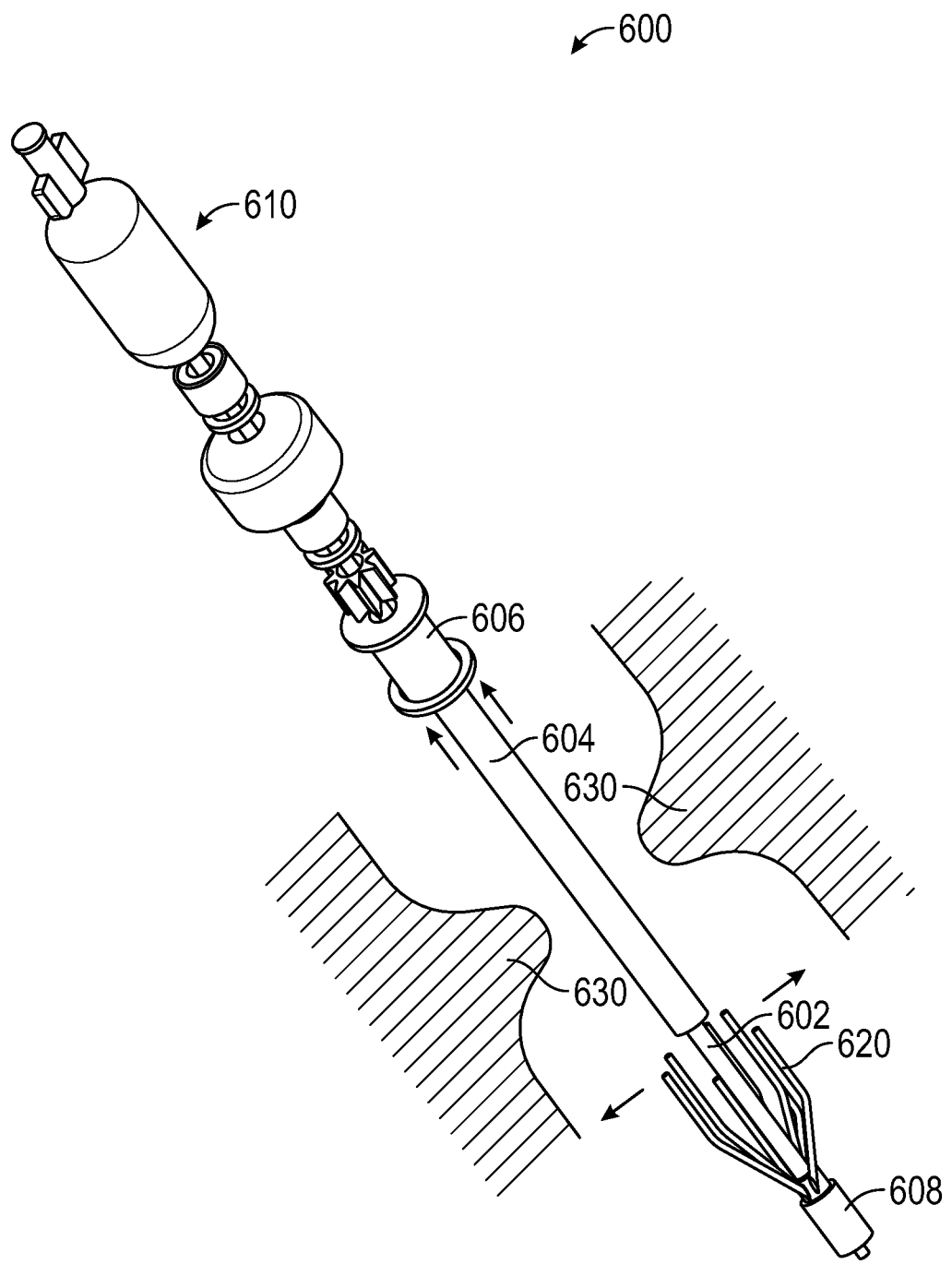
FIG. 21 shows the device of FIG. 20 with a needle portion being deployed below the heart valve region, prior to retracting the device and driving the needles through the native tissue and a prosthetic device (not shown).

FIGS. 20 and 21 illustrate another exemplary suturing device 600 comprising an inner shaft 602, an outer shaft 604, a grip 606 on the outer shaft, a distal head 608 coupled to the distal end of the inner shaft at the distal end of the outer shaft, and a proximal portion 610 coupled to the proximal end of the inner shaft. As shown in FIG. 20, the distal head 608 can initially be inserted through a native valve annulus 630. As shown in FIG. 21, the grip 606 can then be used to retract the outer shaft 604, which exposes an array of needles 620 that extend proximally from adjacent the distal head

608. The needles 620 can resiliently pop radially outwardly to a preset functional position matching the size of the annulus 630. The device 600 can then by pull back proximally to drive the needles 620 through the annulus in unison. An annular prosthetic device can be positioned on the proximal side of the annulus and the needles 620 can be driven through the prosthetic device after passing through the annulus. Each needle 620 can guide a suture (e.g., within hollows inside the needles) through the annulus and through he prosthetic. The other end of the sutures can run up through the inner shaft to the proximal portion 610 of the device.

In any of the disclosed suturing device embodiments, the total number of curved needles and/or straight needles can vary according to the suturing needs of the given prosthetic device. In some cases, just a two or three or four sutures may be sufficient, and thus just many of each of needles may be included in the suturing device. For larger, more robust prosthetic devices, such as a prosthetic aortic valve for a large man, 10, 12, 14, 16, 18, 20 or more sutures may be needed to secure the device to the native tissue, and a corresponding number of each type of needles can be included in the suturing device. The can be the same number of curved needles as the straight needles, so that they are arranged in pairs of one of each kind of needle for each suture. The needles can be arrayed around the suturing device in a shape that matches the shape of the native structure and/or the prosthetic device, such as a circular array, an oval-shaped array, a D-shaped array, a kidney-shaped array, a C-shaped array, etc. In some embodiment the prosthetic device can be only partially annular, such as a C-shaped annuloplasty ring, (such embodiments are still considered "annular prosthetic devices" as that term is used herein) and the needles of the suturing device can be arrayed in a correspondingly similar configuration.

Some embodiments that fall within the scope of the disclosed technology include needles that are oriented and/or move in directions generally reverse of the embodiments disclosed in the figures and above. For example, in such embodiments, the curved needles can curve upwardly/proximally when penetrating through the native tissue, rather than downwardly/distally. The straight needles (if included) may also move proximally first to penetrate the annular prosthetic device, and then retract back distally. By reversing the needle motion, the device can suture a prosthetic device in place from the opposite side of the native valve annulus. For example, an annular prosthetic device can be sutured to an inferior/distal side of an aortic valve annulus with the suturing tool still be deployed from the superior/proximal side. For example, the suturing device and prosthetic device can pass distally through the native valve orifice first before suturing in such embodiments, then with the prosthetic device in place, the curved needles can be deployed to penetrate up/proximally through the native tissue. The straight needles, if included, can project up/proximally from a plate on the suturing device and can pass upwardly/proximally through the prosthetic device (e.g., a sewing ring) to meet with the tips of the curved needles to engage the sutures on the proximal side the device and pull the sutures back down distally through the prosthetic device.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, or otherwise linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined. In the context of the present application, the terms "lower" and "upper" are used interchangeably with the terms "proximal" and "distally", respectively. Thus, for example, the lower or bottom side of a device is its distal side and the upper or top side of the device is its proximal side.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. We therefore claim all that falls within the scope and spirit of these claims.

What is claimed is:

1. A suturing device for suturing an annular prosthetic device within a native heart valve region, the device comprising:
   a shaft portion defining a shaft axis;
   a handle portion at a proximal end of the shaft portion, the handle portion including an actuator; and
   a suturing portion at a distal end of the shaft portion, the suturing portion including curved needles arrayed around the shaft axis and straight needles arrayed around the shaft axis;
   wherein the straight needles and the curved needles are configured to guide a plurality of sutures; and
   wherein the actuator causes the straight needles to move axially relative to the curved needles and causes the curved needles to rotate, such that the axial motion of the straight needles and the rotation of the curved needles are coordinated to simultaneously place the plurality of sutures that secure the annular prosthetic device within the native heart valve region.

2. The suturing device of claim 1, wherein the annular prosthetic device comprises a prosthetic heart valve.

3. The suturing device of claim 1, wherein the annular prosthetic device comprises an annuloplasty ring.

4. The suturing device of claim 1, wherein the native heart valve is a native aortic valve.

5. The suturing device of claim 1, wherein the straight needles project distally from a first rigid support plate.

6. The suturing device of claim 1, wherein the straight needles comprise hooks at their distal ends.

7. The suturing device of claim 1, wherein the straight needles penetrate the annular prosthetic device when the actuator causes the straight needles to move axially relative to the curved needles.

8. The suturing device of claim 1, wherein the curved needles each project from a respective drive shaft, and the curved needles each rotate about an axis of their respective drive shaft.

9. The suturing device of claim 8, wherein the drive shafts are all supported by a second rigid plate, such that the drive shafts can each rotate about their respective axis relative to the second rigid plate.

10. The suturing device of claim 9, wherein the straight needles pass through openings in the second rigid plate.

11. The suturing device of claim 8, wherein the drive shafts are all engaged to a common central driver, wherein the central driver causes the drive shafts and the curved needles to rotate.

12. The suturing device of claim 8, wherein the plurality of sutures pass through the drive shafts and through the curved needles.

13. The suturing device of claim 1, wherein the curved needles guide the plurality of sutures through tissue in the native heart valve region and adjacent to the annular prosthetic device when the curved needles rotate.

14. The suturing device of claim 1, wherein the straight needles engage the plurality of sutures and pull the sutures proximally from the curved needles through the annular prosthetic device.

15. The suturing device of claim 1, wherein the curved needles are configured to guide sutures proximally through the native tissue as they rotate.

* * * * *